United States Patent
Moufle et al.

[11] Patent Number: 6,138,515
[45] Date of Patent: Oct. 31, 2000

[54] APPARATUS FOR THE ACOUSTIC DETECTION OF DEFECTS IN A MOVING STRIP

[75] Inventors: Jean-Pierre Moufle, Seraincourt; Philippe Piquemal, Silly-sur-Nied, both of France

[73] Assignee: Sollac, France

[21] Appl. No.: 09/101,796

[22] PCT Filed: Mar. 7, 1997

[86] PCT No.: PCT/FR97/00403

§ 371 Date: Nov. 17, 1998

§ 102(e) Date: Nov. 17, 1998

[87] PCT Pub. No.: WO97/33167

PCT Pub. Date: Sep. 12, 1997

[30] Foreign Application Priority Data

Mar. 8, 1996 [FR] France ................................ 96 02913

[51] Int. Cl.⁷ .......................... G01N 29/06; G01N 29/26
[52] U.S. Cl. .................. 73/639; 73/644; 73/159
[58] Field of Search ............................ 73/639, 635, 636, 73/644, 598, 600, 620, 627, 629, 159

[56] References Cited

U.S. PATENT DOCUMENTS

| | | | |
|---|---|---|---|
| 2,992,553 | 7/1961 | Joy | 73/634 |
| 3,028,753 | 4/1962 | Joy | 73/634 |
| 3,616,684 | 11/1971 | Nusbickel, Jr. | 73/644 |
| 3,628,374 | 12/1971 | Laudien et al. | 73/639 |
| 4,928,707 | 5/1990 | Kliesch | 73/644 |
| 5,313,837 | 5/1994 | Haynes | 73/622 |
| 5,404,755 | 4/1995 | Olson et al. | 73/639 |
| 5,505,089 | 4/1996 | Weigel | 73/635 |

FOREIGN PATENT DOCUMENTS

| | | |
|---|---|---|
| 2570502 | 3/1986 | France . |
| 2582814 | 12/1986 | France . |
| 1949586 | 6/1970 | Germany . |
| 33 30 069 | 2/1984 | Germany . |

*Primary Examiner*—Hezron Williams
*Assistant Examiner*—Rose M. Miller
*Attorney, Agent, or Firm*—Nixon Peabody LLP; Thomas W. Cole

[57] ABSTRACT

An apparatus for detecting defects in a moving cast metal strip is provided that includes at least one Lamb-wave transducer housed inside a sensor wheel made of flexible material. The sensor wheel contains an acoustic coupling fluid and is designed to come into running contact with the surface of the product to be inspected. A runner is placed upstream of the sensor wheel for contact with the surface of the strip to be inspected. Upstream of the runner, a delivery system for delivering coupling fluid onto the surface of the moving product is provided, this fluid serving to wet the surface of the strip. The runner includes a roller having a contact width the same or greater than the width of the product for uniformly spreading the coupling fluid over the product. All of these components are installed in a movable carriage which is designed to run over the metal strip surface. The apparatus is capable of detecting defects in a steel strip moving at high speed.

8 Claims, 1 Drawing Sheet

APPARATUS FOR THE ACOUSTIC DETECTION OF DEFECTS IN A MOVING STRIP

BACKGROUND OF THE INVENTION

The present invention relates to the non-destructive control of moving products, especially a steel strip in the course of its manufacturing process in the iron-and-steel industry.

More specifically, the invention relates to the ultrasonic detection of defects in such a strip by subjecting it to guided vibratory waves, for example so-called Lamb waves.

Lamb waves are ultrasonic vibrations which propagate in the thickness of the product to be inspected, being guided by opposed plane faces of the product. In the case of flat products, such as a metal strip, the waves, channeled by the two parallel plane faces of the product to be inspected, propagate transversely to the direction of movement, and therefore along the width of the strip, from a point of emission, chosen for placing the transducer, to an edge where they are reflected, thereby producing a strong echo signal. Any defect, for example a nonmetallic inclusion, present in the strip or emerging on the surface thereof during passage of the wave represents a local discontinuity of the material transversed which responds with a signal, the intensity of which depends on the size and nature of the defect and the moment of appearance of which, between the emission echo and the edge echo, is representative of the point on the strip where the defect occurs.

The industrial practice is generally to use two transducers, arranged one after the other in the direction of movement of the strip. Each transducer is placed near a different edge of the strip and emits in the direction of the opposite edge. In this way, the strip is scanned twice in a short time interval and in opposite directions, thereby improving the reliability of the results of the analysis, as well as coverage of the area probed.

DESCRIPTION OF THE PRIOR ART

According to a known embodiment to which the invention relates, the transducer is housed inside a hollow wheel made of flexible material, filled with an acoustic coupling fluid (in general, water). This sensor wheel comes into running contact when pressed against the moving strip, thus ensuring that there is, in front of the transducer, a thickness of coupling fluid permanently matched to the distance which separates the transducer from the strip.

In general, provision is made for the bearing force of the wheel to be adjusted in order to allow intimate contact with the strip and thus to reduce the acoustic interface effect. However, an external supply of lost coupling fluid having good wetting properties, for example mineral oil, is always provided between the wheel and the strip in order to ensure perfect coupling at this interface. However, it seems that the known apparatuses of this type are now reaching their limit of use. This is because the results that they give as the speed of movement of the strip exceeds 100 m/min., as is very often the case in modern plants, quickly degenerate, or even become unusable.

SUMMARY OF THE INVENTION

The object of the present invention is to achieve defect detection in products moving at high speed, of the order of 500 or 600 m/min., or even higher.

For this purpose, the subject of the invention is an apparatus for the acoustic detection of defects in a moving product, such as a steel strip during its production, comprising at least one guided-wave (Lamb-wave) ultrasonic transducer housed inside a sensor wheel made of flexible material, which contains an acoustic coupling fluid and is designed to come into running contact with the surface of the product to be inspected, which apparatus is distinguished by the fact that it has, on the one hand, a runner for contact with the surface of said product, placed upstream of the sensor wheel in the direction of movement of the product, and, on the other hand, upstream of said runner, a controlled delivery of lost coupling fluid onto the surface of the moving product.

Advantageously, the runner has a well-ground and non-deformable contact surface in order to be able to bear on the surface of the product to be inspected. Preferably, the width of this surface is the equal to or greater than that of the sensor wheel.

Advantageously, the runner consists of a roller.

DESCRIPTION OF THE PREFERRED EMBODIMENT

In a preferred embodiment, the sensor wheel and its associated runner are placed on a movable carriage designed to be placed on the surface of the moving product to be inspected and guided by a support device which determines its position over the width of said product.

As doubtless will already have been understood, the invention essentially resides in the fact that a runner in contact with the surface of the strip to be inspected is placed in front of the sensor wheel containing the sensor and in that, in front of this runner, a flow of coupling fluid is delivered onto the strip, the natural spreading of the fluid, before the wheel passes over it, will be forced and regularized by the action of the runner. In addition, the latter, by virtue of the pressure that it exerts on the strip, will improve the wetting of the surface by the infractuosities of the latter, which distinguish its roughness, being finely impregnated. Consequently, any tendency to form areas or mini-pockets of air on the surface of the strip which are deleterious to the transmission of the ultrasonic energy during passage of the sensor wheel are counteracted.

Thus, it may be clearly established that, prior to the passage of the sensor wheel, the quality of the wetting the surface of the coupling fluid, achieved according to the invention was the determining factor guaranteeing reliable defect detection at high speeds of movement. Of course, the reproducibility of the results obtained will also depend on keeping the coupling fluid at a constant viscosity, and therefore at a constant temperature, and likewise keeping the thickness of the film of fluid at the surface of the strip as uniform as possible.

DESCRIPTION OF THE DRAWINGS

The invention will be well understood and other aspects and advantages will appear more clearly in light of the following description given by way of example, with reference to the appended plates of drawings, in which.

In the figures, the same elements are denoted by identical references.

Figure 1:
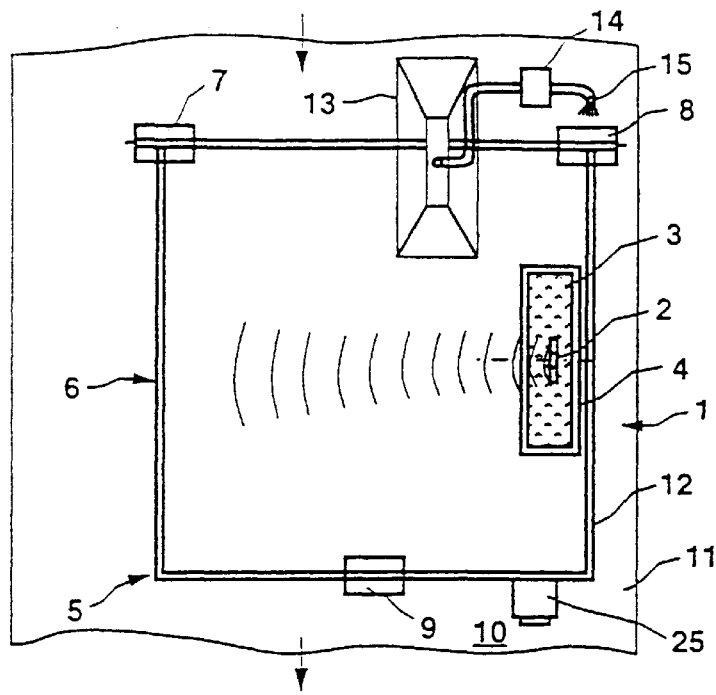
FIG. 1 represents a diagrammatic top view of a detection apparatus according to the invention.

As may be seen in these figures, a sensor wheel 1, consisting of a water-swelled elastomeric tire, contains the Lamb-wave ultrasonic transducer 2 immersed in this mass of water 3, the function of which is to ensure ultrasonic coupling between the sensor 2 and the cover 4 of the wheel.

The transducer 2 used may be of the piezoelectric type. It is fitted with a set inclination of its emission head with respect to the plane of the surface 10 of the strip 11 to be inspected so as to generate, within this strip, Lamb waves propagating in the transverse direction of the strip toward an edge.

The wheel 1 is mounted on a movable carriage 5 provided with a chassis 6 which has three castors 7, 8 and 9 arranged in a triangle in order to ensure the correct attitude of the carriage as it runs over the strip 11 to be inspected, this strip moving in the direction indicated by the straight arrows. Two castors, 7 and 8, are placed at the ends of the front face of the chassis, the third, 9, is positioned midway along the near face.

As may be seen, the sensor wheel 1 has been mounted here so as to be offset on the chassis on a side face 12 of the latter. This side face 12 is chosen as being that which will be close to that edge of the strip which is opposite that toward which the train of ultrasonic waves delivered by the transducer 2 will be directed. It will be understood that this offset represents a particularly advantageous arrangement allowing the entire width of the strip 11 to be scanned, to within the thickness of the wheel 1, as long as the carriage 5 is positioned as close as possible to the edge of the strip, as is the case in FIG. 1.

The diameter of the sensor wheel 1 is appreciably greater than that of the castors so that it intentionally extends, toward the bottom of the carriage, a few millimeters beyond the limit of the castors when the carriage is not bearing on the strip.

The equipment of the carriage also comprises an on-board reservoir 13 which, by means of a servovalve 14, supplies the delivery pipe 15 with the lost coupling fluid [having the property of wetting the steel surface 10 well (the fluid being a mineral oil, for example)], this delivery pipe 15 being designed to deliver an adjusted flow onto this surface at the point where the sensor wheel 1 passes.

A spreader runner for this lost fluid, fastened to the carriage 5, is provided on the line along which the sensor wheel 1 passes, upstream of the latter in the direction of movement of the strip 11. In the embodiment described, this spreader runner advantageously consists of the castor 8 itself.

In order for the forced spreading area of this wetting fluid to be compatible with the size of the area of contact between the wheel 1 and the strip, the useful width of the runner 8 will preferably be equal to or even greater than that of the cover 4 of the wheel, on account of its deformation caused by the squashing action.

Figure 2:
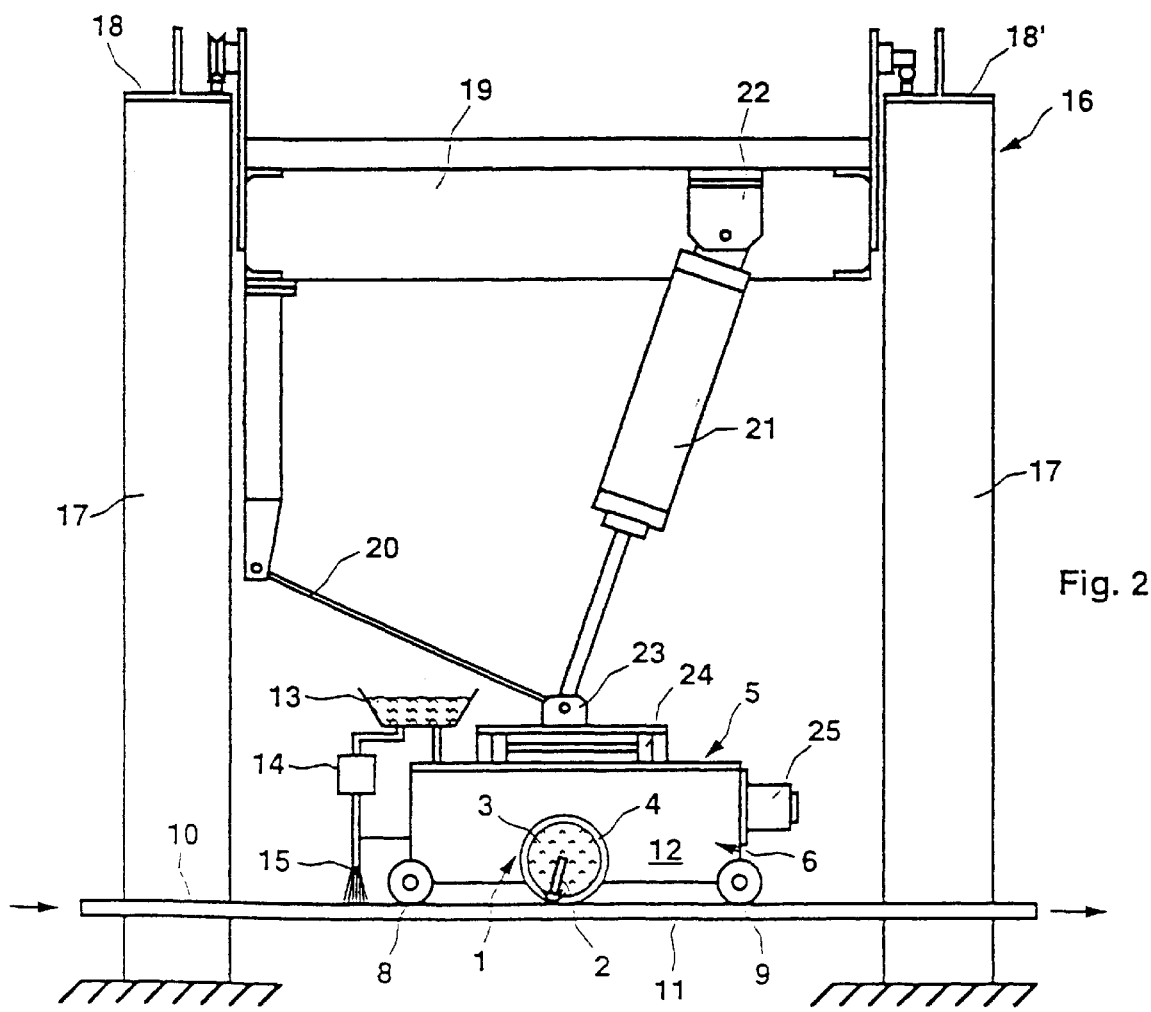
FIG. 2 represents a diagrammatic side view of the apparatus.

The carriage 5 is positioned over the width of the strip 11 by guiding equipment 16, which is only visible in FIG. 2. This equipment comprises a support arm 17 equipped with two rails 18, 18' on which a bridge 19 moves translationally in the direction of the width of the strip 11. This bridge supports the movable carriage 5 by means of a pneumatic suspension comprising an articulated arm 20 and a cylinder 21, the upper end of which is pivoted to a "U" clamp 22 fixed to the bridge 19, and the other end of which joins the end of the arm 20, at the same point of attachment, to a clevis 23 located on the top of the carriage.

The suspension system ensures that the sensor 1 is in permanent contact with and guided over the surface 10 of the strip to be inspected, while at the same time limiting the force exerted on the latter to a few kilograms, for example. For this purpose, a counterpressure may be supplied in the cylinder in order to provide partial compensation for the weight of the carriage 5.

The position of the transducer 2 over the width of the strip 11 can be adjusted by moving the carriage 5 in two steps: firstly, by moving the bridge 19 and then, more finely, with the aid of a "screw-nut" pair 24 driven by a motor (not shown) and providing the mechanical linkage between the clevis 23 and the carriage 5 itself.

The distance between the transducer and the surface of the strip 11 may be between 5 and 15 mm, for example, depending on to what extent the elastomeric cover 4 of the sensor wheel is squashed. This extent of squashing may be adjusted by inserting, for example, a shim between the axle of the sensor wheel 1 and the chassis of the carriage which holds it in place so as to set the downward projection of the wheel beyond the limits of the castors.

As is known, the angular position of a Lamb-wave transducer, such as the sensor 2, is defined by its two angles of incidence, which are measured with respect to the normal to the surface of the strip to be inspected, one in a plane parallel to the direction of movement and the other in a plane perpendicular to this direction. Conventionally, these angles are set respectively between $-20°$ and $+20°$ and between 0 and $45°$. The corresponding settings may be achieved from outside the wheel 1 by means of standard screw-nut systems driven by a stepper motor 25 mounted on board the carriage itself.

In order to keep these angles as constant as possible, whatever the movements of the moving strip 11 (undulations, roll, etc.), the carriage 5 is pivoted at its point of attachment to the clevis 23 to the rod of the cylinder 21 along two perpendicular axes, in the manner of a universal joint.

As already mentioned, in the embodiment illustrated in the figures the sensor wheel 1 is in an offset position on one side of the frame forming the chassis of the carriage 5.

There are two advantages of this arrangement. Firstly, it allows the wheel to be located at an extreme edge of the strip so as thus to be able to scan almost the entire width of the strip 11 with the train of Lamb waves emitted by the transducer. Furthermore, it has the advantage of making one of the castors, in this case the castor 8, act as the spreader runner present upstream of the sensor wheel 1, in accordance with an essential characteristic of the invention.

The spreading effect of the coupling wetting fluid, discharged by the delivery means 15, and the thickness uniformity of the spread film after it has passed under the runner 8 are enhanced by the fact that the runner has a rigid, nondeformable and well-ground surface for contact with the strip 11. Under these conditions, a moderate bearing force, of the order of 1 kg, is sufficient so that the runner also forces the coupling fluid to penetrate into the slightest asperities in the surface of the strip, somewhat like a compressor roller on a freshly bituminized roadway.

The air micropockets, which would naturally tend to be left trapped in the infractuosities of the surface 10 under the skin of coupling fluid are thus avoided, because of the expulsion effect of the passage of the runner 8. This results in optimum wetting of the surface by the coupling fluid at the wheel/strip interface, which is a guarantee that the invention can be employed on a rapidly moving product. The invention may thus be applied without any particular difficulty to a steel strip in the process of being produced, for example at the output of a pickling line before rerolling, although the speed of the product at this point is conventionally between 400 and 600 m/min.

It will be noted that the single-transducer device described above allows up to 60–70% of a 120 cm wide strip to be probed, knowing that the end areas are in any case unusable because of the emission echoes (approximately 25 cm) and the edge echoes (from 5 to 10 cm). This percentage may be increased further by using two sensor wheels placed one after the other, but on different edges, and therefore emitting wave trains scanning the strip in opposite directions.

It goes without saying that the invention is not limited to the device exemplified, but extends to many variants or equivalents, as long as the definition of the invention given by the appended claims is respected.

In particular, it will be noted that although the spreader runner 8 is preferably a roller this embodiment is not the only one possible. A simple brush, or a flat rubbing runner acting in this case in the manner of a doctor at the surface of the strip, could also be suitable for spreading the coupling fluid.

Likewise, the uniformity of the detection results will be enhanced if care is taken to ensure that the viscosity of the acoustic coupling fluid discharged onto the strip is constant. This means that measures will be taken to keep its composition constant, by means of a reservoir 13 of sufficient capacity, and also to keep its temperature constant by providing, if necessary, regulated heating means within the reservoir 13, for example.

The invention applies not only to moving strips, plates or other flat products but also to any product, whatever its shape, as long as plane faces delimit the part to be probed.

Likewise too, although the invention finds its optimum use for steel products, because of the low damping of the Lamb waves in this material, other materials, for example metallic materials such as copper or aluminum, or even nonmetallic materials, may, without any particular difficulties, benefit therefrom as long as the possible defects sought represent large enough acoustic discontinuities within the material traversed by the waves in order to produce echoes detectable by the sensor.

Moreover, the invention is not limited to the use of Lamb waves but may be suitable for the use of another type of guided-wave ultrasonic transducer used for inspection of products undergoing relative movement.

What is claimed is:

1. An apparatus for the acoustic detection of defects in a moving metal strip during its production, comprising
    at least one guided-wave sonic transducer;
    a sensor wheel made of flexible material for housing said transducer, said wheel containing an acoustic coupling fluid and having a cover for running contact with a surface of a metal strip;
    a runner for contact with the surface of the strip placed upstream of the sensor wheel in the direction of movement of said strip, said runner including a roller having a non-deformable contact surface for bearing on the surface of the strip, and a contact width equal to or greater than that of a width of the cover of the sensor wheel in contact with the strip, and;
    a mechanism for providing a controlled delivery of coupling fluid onto the surface of the strip for wetting said surface of said strip in front of said runner.

2. The apparatus as claimed in claim 1, wherein the sensor wheel, the runner and the mechanism for providing a controlled delivery of wetting coupling fluid are mounted on a movable carriage designed to run over the surface of the moving strip, and further comprising devices for supporting and guiding said carriage and determining its position over a width of said strip.

3. The apparatus as claimed in claim 2, wherein the movable carriage is mounted on castors and one of said castors constitutes the runner.

4. The apparatus as claimed in claim 2, wherein the sensor wheel is mounted in an offset position on the carriage.

5. The apparatus as claimed in claim 2, wherein the carriage is provided with an on-board reservoir connected to the controlled delivery mechanism for containing the wetting coupling fluid.

6. The apparatus as claimed in claim 2, further comprising a servovalve associated with the controlled mechanism delivery for adjusting a flow of wetting coupling fluid discharged from the runner onto the surface of the strip.

7. The apparatus as claimed in claim 2, wherein the devices for supporting and guiding the carriage comprise an adjustment assembly for making fine adjustment of a position of the carriage on the surface of the strip.

8. An apparatus for the acoustic detection of defects in a moving metal strip during its production, comprising:
    at least one guide-wave sonic transducer;
    a sensor wheel made of flexible material for housing said transducer, said wheel containing an acoustic coupling fluid and having a cover for running contact with a surface of a metal strip;
    a mechanism for providing a controlled delivery of coupling fluid onto the surface of the strip for wetting said surface of said strip, and
    a runner for contact with the surface of the strip placed upstream of the sensor wheel in the direction of movement of said strip and downstream of said coupling fluid delivery mechanism,
    said runner including a roller means having a non-deformable contact surface for bearing on the surface of the strip and for uniformly spreading said coupling fluid across the surface of the strip.

* * * * *